United States Patent
Pfanner

(10) Patent No.: US 10,905,593 B2
(45) Date of Patent: Feb. 2, 2021

(54) EAR PROTECTION DEVICE, COMMUNICATIONS SYSTEM AND PROTECTIVE HELMET

(71) Applicant: PFANNER SCHUTZBEKLEIDUNG GMBH, Koblach (AT)

(72) Inventor: Anton Pfanner, Hohenems (AT)

(73) Assignee: PFANNER SCHUTZBEKLEIDUNG GMBH, Koblach (AT)

( * ) Notice: Subject to any disclaimer, the term of this patent is extended or adjusted under 35 U.S.C. 154(b) by 202 days.

(21) Appl. No.: 16/068,203

(22) PCT Filed: Dec. 20, 2016

(86) PCT No.: PCT/EP2016/081978
§ 371 (c)(1),
(2) Date: Jul. 5, 2018

(87) PCT Pub. No.: WO2017/118571
PCT Pub. Date: Jul. 13, 2017

(65) Prior Publication Data
US 2019/0021910 A1    Jan. 24, 2019

(30) Foreign Application Priority Data
Jan. 4, 2016  (DE) .................. 10 2016 100 086

(51) Int. Cl.
*H04R 1/00* (2006.01)
*A61F 11/14* (2006.01)
(Continued)

(52) U.S. Cl.
CPC ................ *A61F 11/14* (2013.01); *A42B 3/16* (2013.01); *A42B 3/30* (2013.01); *H04R 1/04* (2013.01);
(Continued)

(58) Field of Classification Search
CPC ............ H04R 2201/107; H04R 1/1008; H04R 1/1066; H04R 1/1041; H04R 5/033; H04R 5/0335
See application file for complete search history.

(56) References Cited

U.S. PATENT DOCUMENTS 6,236,969 B1 * 5/2001 Ruppert .................. H04M 1/05
704/270
2007/0226865 A1   10/2007 Lindgren
(Continued)

FOREIGN PATENT DOCUMENTS

CN   102281842     12/2011
CN   203608333 U    5/2014
(Continued)

OTHER PUBLICATIONS

International Search Report dated Apr. 10, 2017 by the European Patent Office in International Application No. PCT/EP2016/081978; official translation provided.
(Continued)

*Primary Examiner* — Matthew A Eason
(74) *Attorney, Agent, or Firm* — Hassan Abbas Shakir; Shakir Law PLLC

(57) ABSTRACT

An ear protection device for hearing protection and for fastening to a protective helmet includes a housing with a bearing device, via which it is pivotably mounted in a forklike supporting bracket. A communications device is arranged in the housing and the bearing device has at least two electrically conductive contact elements. A communications system is joined to a protective helmet.

18 Claims, 6 Drawing Sheets

(51) Int. Cl.
*A42B 3/16* (2006.01)
*A42B 3/30* (2006.01)
*H04R 1/04* (2006.01)
*H04R 1/10* (2006.01)

(52) U.S. Cl.
CPC ...... *H04R 1/1008* (2013.01); *A61F 2011/145* (2013.01); *H04R 2420/07* (2013.01)

(56) References Cited

U.S. PATENT DOCUMENTS

| | | |
|---|---|---|
| 2011/0209273 A1 | 9/2011 | Fountain et al. |
| 2013/0219598 A1 | 8/2013 | Pfanner et al. |

FOREIGN PATENT DOCUMENTS

| | | |
|---|---|---|
| CN | 204104947 U | 1/2015 |
| CN | 204575970 U | 8/2015 |
| DE | 1259390 B | 1/1968 |
| DE | 102005003545 A1 | 8/2006 |
| DE | 202011000212 U1 | 5/2011 |
| DE | 102010026997 A1 | 1/2012 |
| JP | 3015953 U | 9/1995 |
| JP | H10129511 A | 5/1998 |
| JP | 2005072703 A | 3/2005 |
| WO | 2010/022440 | 3/2010 |
| WO | 2015108854 A1 | 7/2015 |

OTHER PUBLICATIONS

Written Opinion dated Jul. 13, 2017 by the European Patent Office to WIPO Patentscope in International Application No. PCT/EP2016/081978; official translation provided.

Office Action dated Jul. 27, 2016 by the German Patent Office in German Patent Application 10 2016 100 086.8, partial machine translation provided.

"Examination report No. 1 for standard patent application" issued in related Australian patent application 2016384697 dated Oct. 15, 2018 by IP Australia.

"Notification of First Office Action" issued in related Chinese patent application 201680077859.X dated Apr. 9, 2020 by the China National Intellectual Property Administration, translation provided.

"Notice of Submission of Argument" issued in related Korean patent application 10-2018-7021293 dated Dec. 28, 2019 by the Korean Intellectual Property Office, translation provided.

"Notification of Grounds for Rejection" issued in related Japanese patent application 2018-534724 dated Jun. 25, 2019 by the Japanese Patent Office, translation provided.

Office Action issued in related Chilean patent application 18202018 dated May 13, 2019 by the Chilean Patent Office, English language summary and comments provided.

* cited by examiner

EAR PROTECTION DEVICE, COMMUNICATIONS SYSTEM AND PROTECTIVE HELMET

BACKGROUND OF THE INVENTION

1. Field of the Invention

The invention relates to an ear protection device for hearing protection to be fastened to a protective helmet, the ear protection device comprising a housing with a bearing device via which it is pivotably mounted in a forklike supporting bracket. The invention further relates to a communications system as well as a protective helmet.

2. Discussion of the Related Art

A generic ear protection device is known from the DE 10 2010 026 997 A1. The ear protection device constitutes a component of hearing protection for a protective helmet, the mentioned forklike supporting brackets being supported on the protective helmet via a tilting joint and a rotary disk. The hearing protection disclosed in the DE 10 2010 026 997 A1 are characterised in that the ear protection device is pivotable into a parking position within the helmet.

Since the hearing protection of a protective helmet does not only prevent desired sound such as, for example, the noise of tools and machines, from reaching the wearer's ear, but also render communication between the wearers of helmets difficult, it is useful to provide communication means enabling the persons protected by the protective helmets and the hearing protection to communicate with each other even with the hearing protection disposed in the working position. The protective effect of the hearing protection should not be impaired thereby.

SUMMARY OF THE INVENTION

It is an object of the invention to further develop an ear protection device so that it enables communication while maintaining its protective effect. In particular, interfering cable connections should be avoidable here.

Said object is solved by the features of the independent claim. Advantageous embodiments of the invention are indicated in the dependent and parallel claims.

The invention is based on the generic ear protection device in that communication means are disposed in and/or on the housing and that the bearing device includes at least two electrically conductive contact elements. The housing of the ear protection device is, insofar, multifunctional. On the one hand, it constitutes the dimensionally stable component of the ear protection device, it provides for the pivotable support of the ear protection device in the supporting bracket through its bearing device, accommodates communication means, and it is, further, the carrier of electrically conductive contact elements essential for the operation of the communication means.

The invention is further developed in a particularly useful way in that the bearing device includes two spigots integrally formed with the housing and in that the electrically conductive contact elements protrude from openings of the spigots connecting an interior of the housing with an exterior of the housing. This construction can be produced by simply drilling holes into the bearing device formed as spigots integrally formed with the housing of the ear protection device.

Usefully, it is contemplated that the contact elements close the openings of the spigots so as to be dust- and/or liquid-tight. In this way, the electric components within the housing of the ear protection device are protected against detrimental environmental influences.

According to a preferred embodiment of the invention, it may be contemplated that the communication means comprise a loudspeaker disposed in the ear protection device. In this way, the wearer of the ear protection device is enabled to receive information transmitted via the communications system with his or her ear.

Likewise, it is particularly useful that the communication means comprises a microphone disposed on the ear protection device via a microphone attachment. The microphone enables the carrier of the ear protection device to transmit information to the communication means.

In this connection it is particularly useful that the communication means include a transceiver device. The communication means may, based on this, receive signals transmitted from the outside and forward the associated information to the wearer of the ear protection device via the loudspeaker in the ear protection device. In the reverse, the communication means receive signals from the microphone coupled with the communication means. Associated signals which can be received by external communication means will then be output by the transceiver device of the internal communication means.

The invention is further developed in a particularly advantageous way in that the transceiver device is a Bluetooth transceiver. Bluetooth is an industrial standard for data transmission between devices over short distances by radio technology. The transmission is bidirectional and unsusceptible to interferences so that the communications system in connection with the ear protection device according to the invention is particularly comfortable in design. Further, a high level of safety is provided for in this way, whereby the ear protection device according to the invention promotes the safety provided for by the protective helmet.

According to a preferred embodiment of the invention, it is further developed by a battery supplying the communication means with power and rechargeable via the electrically conductive contact elements being provided in the housing. The ear protection device as such may therefore be equipped with all components required by communication means. Specifically, the battery is provided as a temporary power source within the ear protection device. The electrically conductive contact elements on the ear protection device, therefore, only have to render the function of charging contacts available.

Usefully, it is contemplated that control elements and/or display elements for controlling and/or monitoring the communication means are provided on the housing. As control elements, specifically, a button for turning the communication means on and off may be provided. This button may, in addition, serve to couple the Bluetooth transceiver with other Bluetooth transceivers, for example with ones disposed in ear protection devices of other wearers, or also with mobile phones or motor vehicle transceivers. Of course, a separate designated button may be disposed on the housing for this purpose. Further, control elements may be provided for changing the volume of the acoustic signals output by the loudspeaker. Also, control elements may be provided for adjusting the microphone sensitivity. As a display element, in the simplest case, one or more light emitting diodes may be provided which may convey information to the user of the ear protection device by means of light signals as such, the colour of the light signals and/or the time sequence of light signals.

The invention further relates to communication means including an ear protection device according to the invention and a forklike supporting bracket in which the ear protection device is pivotably supported, the supporting bracket providing for an electric connection to the electrically conductive contact elements.

In this connection, it may be contemplated that the supporting bracket is a docking station independent of a protective helmet. The docking station made available in this way may, for example, be made available in a motor vehicle, in an accessories case or in any other place. Specifically, the docking station may be designed so as to be stationary or mobile.

Usefully, it may be contemplated that the docking station is supplied with power by photovoltaic cells. The power supply by means of photovoltaic cells renders the wearer of the protective helmet independent of conventional power sources. Precisely in situations requiring a protective helmet, for example in forest work or at construction sites, power sources are not available offhand so that the power supply by means of photovoltaic cells is particularly advantageous.

Apart from the option that the supporting bracket is a docking station independent of the protective helmet, there is also the option that the supporting bracket is attachable to a protective helmet and is both a docking station as well as a supporting bracket to be used when the protective helmet is in use. In this case, it may be contemplated that the supporting bracket as a whole is removed from the helmet together with the ear protection device to then be connected to a power source. Likewise, it is feasible that a battery is accommodated in an arbitrary place in the helmet, the power required for the operation of the Bluetooth transceiver of the protective helmet then being supplied to the Bluetooth transceiver via the electric contact elements of the ear protection device in use. Likewise, it is possible to equip the protective helmet with an electric interface via which the charging power and/or data can be transferred to the ear protection device.

The invention further relates to a protective helmet comprising at least one forklike supporting bracket for supporting an ear protection device according to the invention, at least one supporting bracket being both a docking station and a supporting bracket to be used while the protective helmet is in use.

In this connection, it may be useful that the protective helmet is equipped with a battery by which a communication device disposed in and/or on the ear protection device can be supplied with power.

Furthermore, it may be advantageous that the protective helmet includes an interface via which it can be supplied with power.

BRIEF DESCRIPTION OF THE DRAWINGS

The invention will now be explained by way of example with reference to the accompanying drawings on the basis of particularly preferred embodiments.

In the following description of the drawings, the same reference numerals denote identical or comparable components.

DETAILED DESCRIPTION OF THE INVENTION

Figure 1:
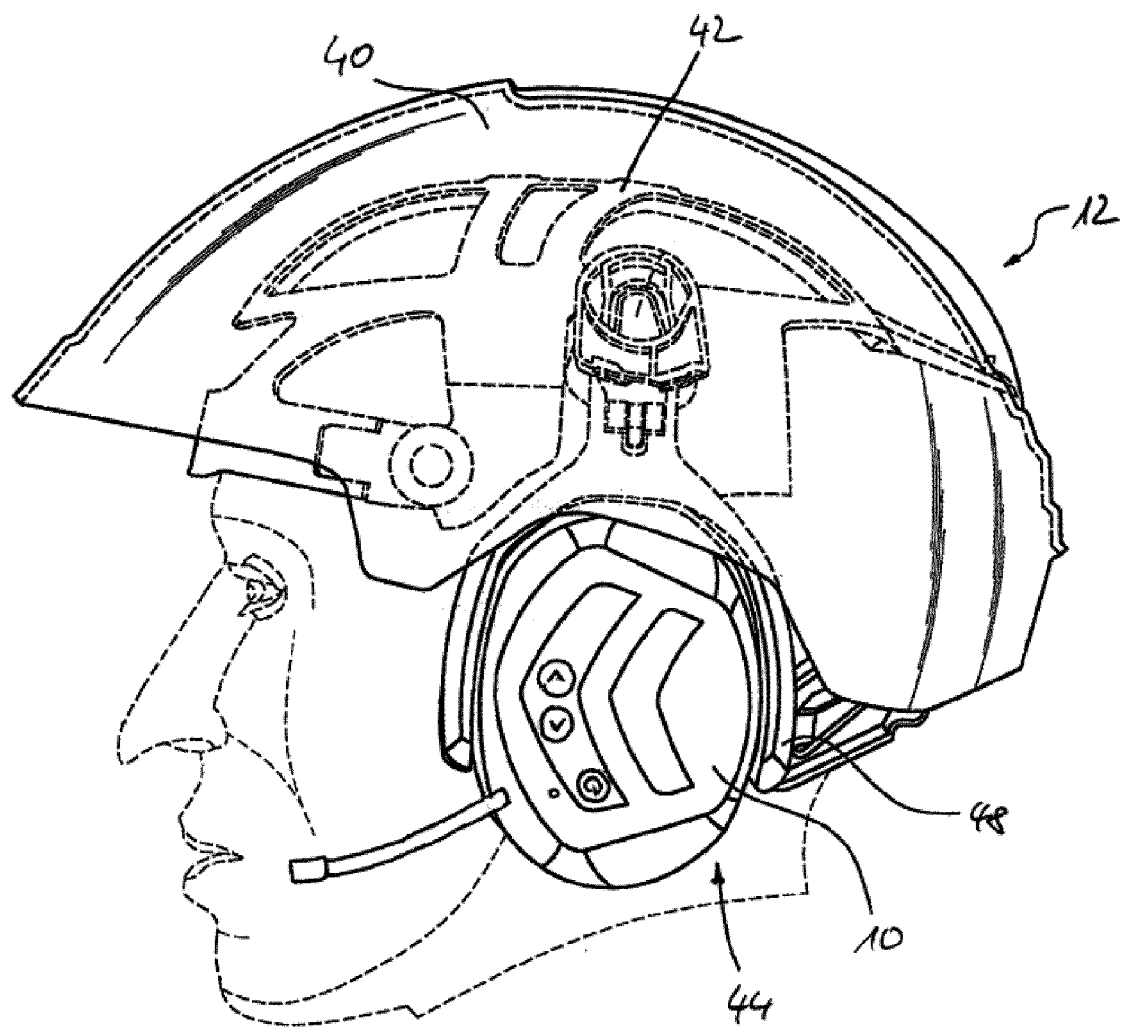
FIG. 1 is a side view of a protective helmet including an ear protection device according to the invention placed on the head of a wearer.

FIG. 1 shows a protective helmet 12 on the head of a wearer. It comprises, among other things, a helmet shell 40, a harness 42, as well as hearing protection 44. The hearing protection 44 comprise at least one ear protection device 10 equipped with communication means 20, 22, 24, 26 in the manner according to the invention. Numerous components of the ear protection device 10 may be allocated to the communication means 20, 22, 24, 26, specifically a loudspeaker 20, a microphone 22, a transceiver device 24, particularly a Bluetooth transceiver, as well as a battery 26. These components are arranged on or in a housing 14 of the ear protection device 10. The ear protection device 10 is supported by a supporting bracket 48.

Figure 2:
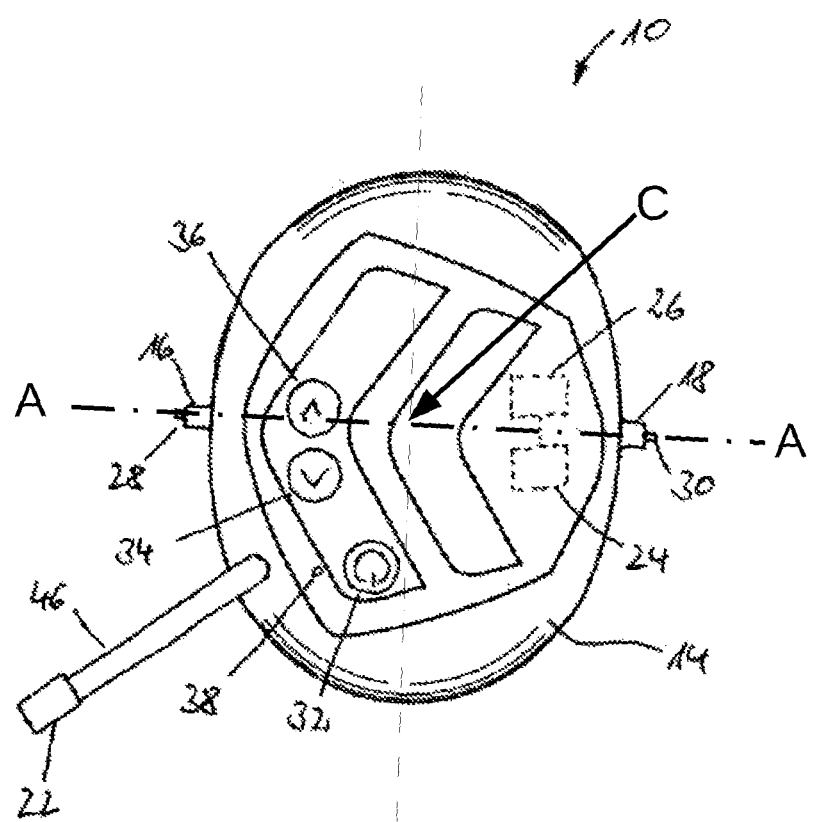
FIG. 2 is a side view of an ear protection device according to the invention.
Figure 3:
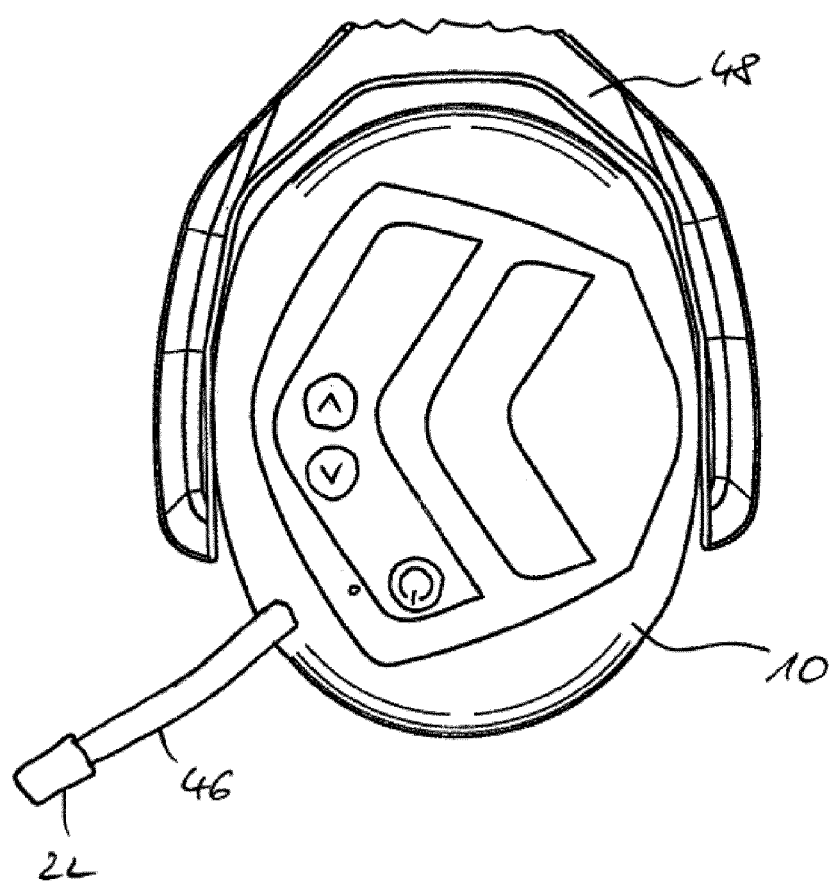
FIG. 3 is a side view of an ear protection device according to the invention in a supporting bracket.
Figure 4:
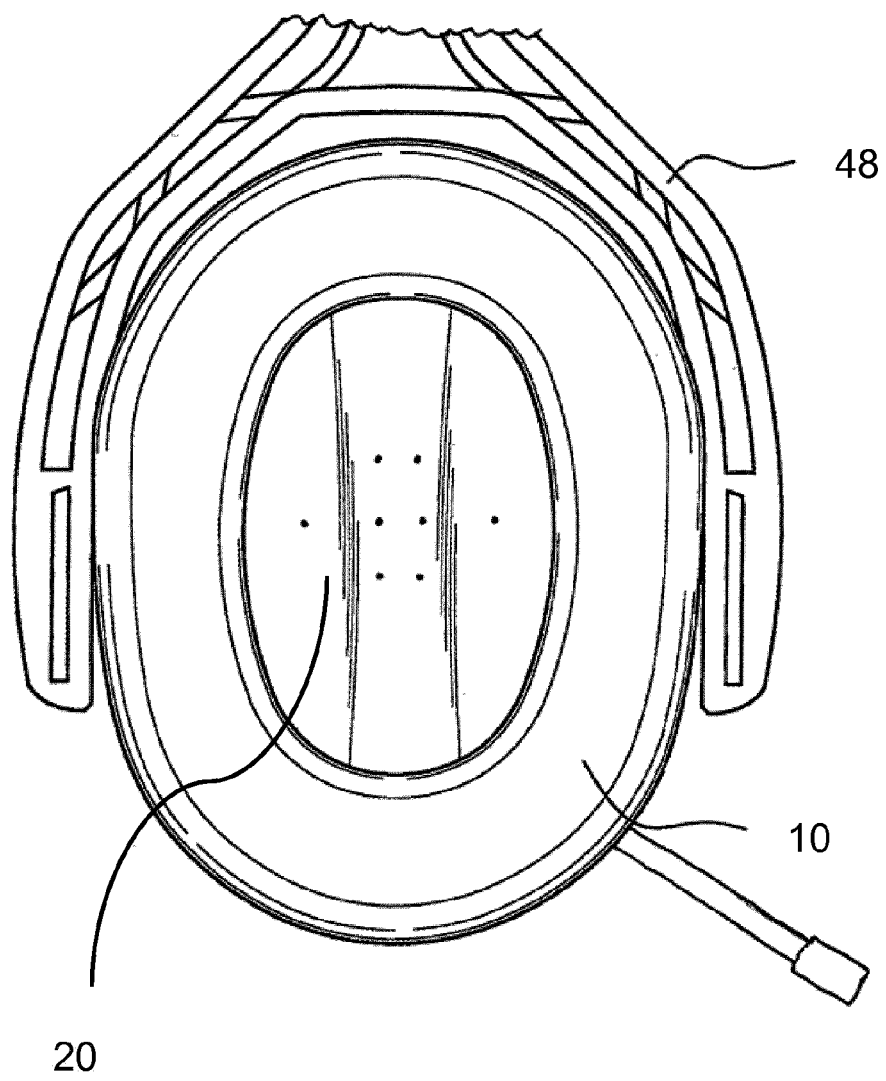
FIG. 4 an interior view of an ear protection device according to the invention in a supporting bracket.
Figure 5:
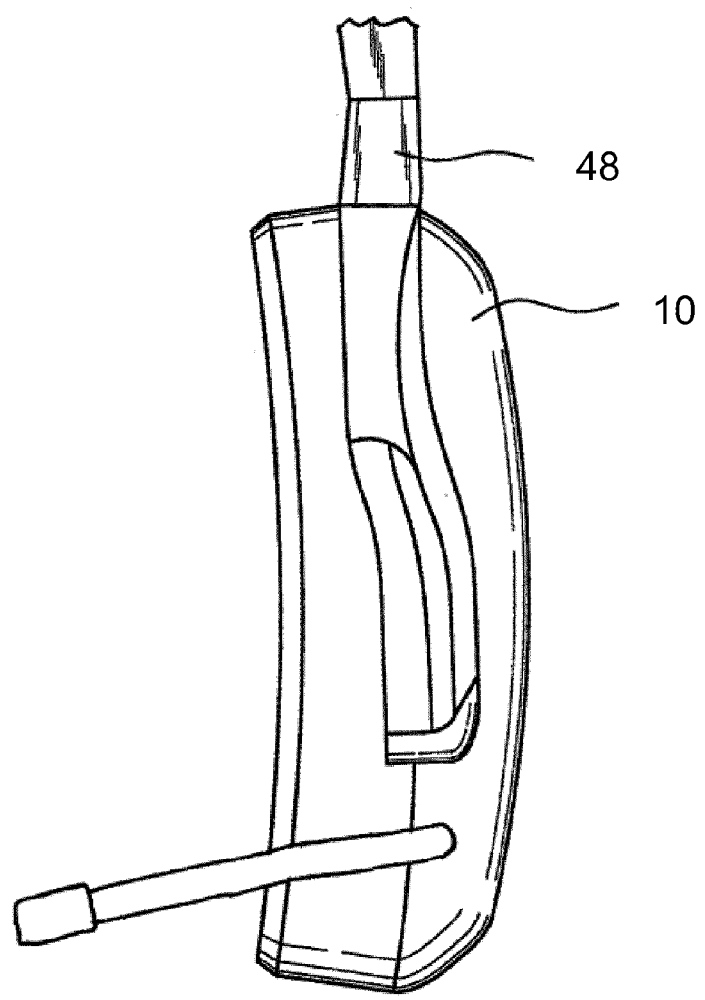
FIG. 5 is a view of an ear protection device according to the invention including a supporting bracket from the front relating to the usual mode of wearing a protective helmet.
Figure 6:
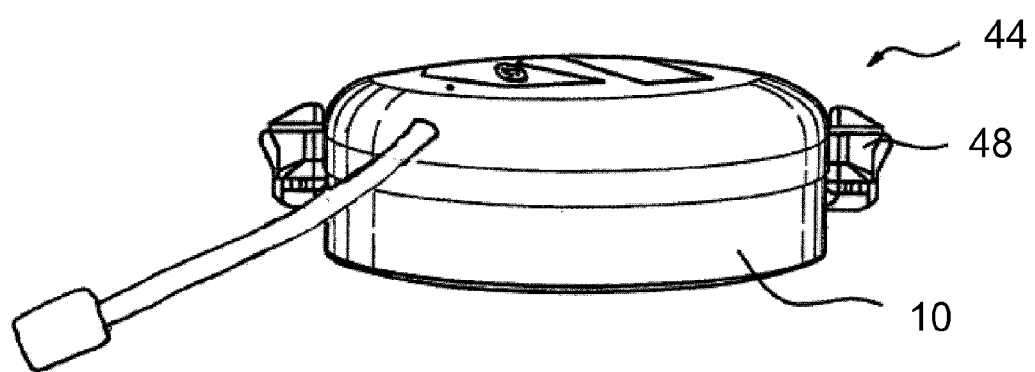
FIG. 6 is a view of ear protection device an according to the invention including a supporting bracket from below relating to the usual mode of wearing a protective helmet.

In FIG. 2, it is indicated by broken lines that the transceiver device 24 as well as the battery 26 are disposed inside of the housing 14 of the ear protection device 10. The microphone 22 is disposed outside of the housing 14 of the ear protection device 10 via a microphone attachment 46. On the outside of the housing 14 of the ear protection device 10, control elements 32, 34, 36 and a display element 38 are disposed. The control elements 32, 34, 36 are buttons. The display element 38 is a light emitting diode. One of the buttons 32 serves to turn on the transceiver device 24 as well as, in case the transceiver device is a Bluetooth transceiver, to pair or couple the Bluetooth transceiver with other external Bluetooth transceivers. Other buttons 34, 36 are provided for changing the volume of the loudspeaker 20 of the ear protection device 10. On the housing 14 of the ear protection device 10, further, a bearing device 16, 18 is provided which is, preferably, realised by spigots 16, 18 integrally formed with the housing 14. These spigots 16, 18 are provided with central holes from which electrically conductive contact elements 28, 30 protrude which connect an interior of the housing to an exterior of the housing. At the same time, these openings close the spigots 16, 18 in dust- and/or liquid-tight manner. For electrically coupling the ear protection device 10 with, specifically, an electric power source, it is inserted into a forklike supporting bracket 48. This supporting bracket 48 may be a docking station independent of the protective helmet 12. However, it may also be contemplated that the supporting bracket is, at the same time, both a docking station and a supporting bracket for use during deployment of the protective helmet 12. In any case, the supporting bracket 48 provides for electric contacts allocated to the electric contact elements 28, 30 of the ear protection device 14 via which the electric power for charging the battery 26 inside the housing 14 of the ear protection device 10 is supplied. It is also possible that the electric contact elements serve to transmit data. This may, for example, be contemplated when a transceiver device is not disposed inside of the housing 14 but outside of it. A further option is that the electric contact elements 28, 30 serve the power transfer to components within of the ear protection device 10 while a battery is disposed outside of the ear protection device 10.

With the communications system thus provided, various types of communication operations can be realised. For example, it is possible to directly couple two ear protection devices with the associated communications systems so that direct communications among the ear protection devices or the wearers of the ear protection devices can be carried out via the ear protection devices. Further, the ear protection devices may be coupled with arbitrary transceiver devices, for example, via the Bluetooth function of a motor vehicle or of a mobile phone. Particularly in case of a coupling with a mobile phone, the carrier of the ear protection device may initiate or accept telephone calls while using the ear protection device. Likewise, it is possible to expand the communication range between two wearers of ear protection devices. On the one hand, this is, of course, possible by coupling both ear protection devices with different telephones and by communication being implemented through a telephone connection between the two telephones and respective Bluetooth data connections between the telephones and the ear protection devices. However, it is also possible to, for example, couple one mobile phone with two ear protection devices. If this mobile telephone is within the reach of both ear protection devices the wearers of the respective ear protection devices can communicate with each other although the distance between them is so that a direct communication between them would no longer be possible.

The at least two electrical contact elements 28, 35 are aligned on an axis A-A passing through a center C of the ear protection device.

The features of the invention disclosed in the above description, the drawings, as well as in the claims may be important for the realisation of the invention both individually as well as in any combination.

LIST OF NUMERALS 10 ear protection device
12 protective helmet
14 housing
16 bearing device/spigots
18 bearing device/spigots
20 loudspeaker
22 microphone
24 transceiver device
26 battery
28 contact element
30 contact element
32 button
34 button
36 button
38 display element
40 helmet shell
42 harness
44 hearing protection
46 microphone attachment
48 supporting bracket

What is claimed is:

1. An ear protection device for hearing protection, the ear protection device being fastenable to a protective helmet, the ear protection device comprising:
a housing, the housing comprising a hearing device, the hearing device for pivotably mounting the ear protection device in a forklike supporting bracket, the hearing device comprising at least two electrically conductive contact elements on opposite sides of the housing; and
a communication device disposed in or on the housing,
wherein the at least two electrical contact elements are aligned on an axis passing through a center of the ear protection device.

2. The ear protection device according to claim 1,
wherein the hearing device comprises two spigots, each spigot being integrally formed with the housing, each spigot comprising an opening,
wherein a respective electrically conductive contact element of the at least two electrically conductive contact elements protrudes from a respective opening of a respective spigot for connection an interior of the housing with an exterior of the housing.

3. The ear protection device according to claim 2, wherein the respective electrically conductive contact element closes the respective opening of the respective spigot to be dust-tight or liquid-tight.

4. The ear protection device according to claim 1, wherein the communication device comprises a loudspeaker disposed in the ear protection device.

5. The ear protection device according to claim 1, wherein the communication device comprises a microphone disposed on the ear protection device via microphone attachment.

6. The ear protection device according to claim 1, wherein the communication device comprises a transceiver device.

7. The ear protection device according to claim 6, wherein the transceiver device is a Bluetooth transceiver.

8. The ear protection device according to claim 1,
further comprising a battery for supplying the communication means with power;
wherein the battery is a rechargeable battery;
wherein the battery is rechargeable via the electrically conductive contact elements; and
wherein the battery is disposed in the housing.

9. The ear protection device according to claim 1,
further comprising a control element for controlling or monitoring the communication device; and
wherein the control element is provided on the housing.

10. A communications system comprising
a forklike supporting bracket;
an ear protection device for hearing protection, the ear protection device being fastenable to a protective helmet, the ear protection device comprising
a housing, the housing comprising a hearing device, the hearing device for pivotably mounting the ear protection device in the forklike supporting bracket the hearing device
comprising at least two electrically conductive contact elements on opposite sides of the housing, and
a communication device disposed in or on the housing; and
wherein the fork-like supporting bracket is an electric connection to the at least two electrically conductive contact elements,
wherein the at least two electrical contact elements are aligned on an axis passing through a center of the ear protection device.

11. The communications system according to claim 10, wherein the supporting bracket is a docking station independent of a protective helmet.

12. The communications system according to claim 10, wherein the docking station is supplied with power by photovoltaic cells.

13. The communications system according to claim 10, wherein the supporting bracket is attachable to a protective helmet and is both a docking station and a supporting bracket for use while the protective helmet is in use.

14. A protective helmet comprising:
- a forklike supporting bracket for supporting an ear protection device; and
- the ear protection device for hearing protection, the ear protection device being fastenable to the protective helmet, the ear protection device comprising
- a housing, the housing comprising a hearing device, the hearing device for pivotably mounting the ear protection device in the forklike supporting bracket, the hearing device comprising at least two electrically conductive contact elements on opposite sides of the housing, and
- a communication device disposed in or on the housing,
- wherein at least one supporting bracket is both a docking station and a supporting bracket for use while the protective helmet is in use,
- wherein the at least two electrical contact elements are aligned on an axis passing through a center of the ear protection device.

15. The protective helmet according to claim 14,
- further comprising a battery for supplying power to the communication device; and
- wherein the power is disposed in or on the ear protection device.

16. The protective helmet according to claim 14, further comprises an interface for supplying the protective helmet power.

17. The ear protection device according to claim 1,
- further comprising a display element for controlling or monitoring the communication device; and
- wherein the display element is provided on the housing.

18. The protective helmet according to claim 15, further comprises an interface for supplying the protective helmet power.

\* \* \* \* \*